(12) United States Patent
Ingle et al.

(10) Patent No.: US 8,469,919 B2
(45) Date of Patent: Jun. 25, 2013

(54) APPARATUS AND METHODS FOR UNIFORMLY DISTRIBUTING COOLANT WITHIN A CRYO-ABLATION DEVICE

(75) Inventors: Frank Ingle, Palo Alto, CA (US); Raphael Hon, Irvine, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1164 days.

(21) Appl. No.: 12/388,399

(22) Filed: Feb. 18, 2009

(65) Prior Publication Data
US 2009/0209949 A1    Aug. 20, 2009

Related U.S. Application Data

(60) Provisional application No. 61/029,825, filed on Feb. 19, 2008.

(51) Int. Cl.
*A61B 18/18* (2006.01)
(52) U.S. Cl.
USPC .................................. 604/23; 604/20; 604/22
(58) Field of Classification Search
USPC .......................................... 604/20–23, 25, 26
See application file for complete search history.

(56) References Cited

U.S. PATENT DOCUMENTS

| | | | |
|---|---|---|---|
| 6,027,499 A | 2/2000 | Johnston et al. | |
| 6,231,543 B1 | 5/2001 | Hegde et al. | |
| 6,235,019 B1 | 5/2001 | Lehmann et al. | |
| 6,355,029 B1 | 3/2002 | Joye et al. | |
| 6,390,185 B1 | 5/2002 | Proeschel | |
| 6,468,297 B1 | 10/2002 | Williams et al. | |
| 6,629,972 B2 | 10/2003 | Lehmann et al. | |
| 6,635,053 B1 | 10/2003 | Lalonde et al. | |
| 7,025,762 B2 | 4/2006 | Johnston et al. | |
| 7,081,112 B2 | 7/2006 | Joye et al. | |
| 7,101,368 B2 | 9/2006 | Lafontaine | |
| 7,150,745 B2 | 12/2006 | Stern et al. | |
| 2003/0060762 A1* | 3/2003 | Zvuloni et al. | 607/96 |
| 2006/0084962 A1 | 4/2006 | Joye et al. | |
| 2009/0118723 A1 | 5/2009 | Lalonde et al. | |

FOREIGN PATENT DOCUMENTS
WO   2006/124184 A1   11/2006

OTHER PUBLICATIONS

PCT International Search Report and Written Opinion for PCT/US2009/034417, forms PCT/ISA/210, 220 and 237, Applicant Boston Scientific Scimed, Inc., dated Jun. 12, 2009 (12 pages).

* cited by examiner

*Primary Examiner* — Nicholas Lucchesi
*Assistant Examiner* — Pritesh Patel
(74) *Attorney, Agent, or Firm* — Seager, Tufte & Wickhem, LLC

(57) ABSTRACT

Apparatus and methods for uniformly distributing coolant within a cryo-ablation device. A nozzle apparatus includes a tubular member having a plurality of angled apertures that induce swirling of coolant streams dispersed through the angled apertures. Coolant swirling round the tubular member and along an inner surface of an inflatable balloon element inflates the balloon element and cryogenically ablate tissue. The swirling action achieved using angled apertures uniformly distributes coolant along the inner surface of the balloon such that the temperatures along an inner surface of the balloon element and ablation of tissue adjacent to the balloon element are substantially uniform.

20 Claims, 16 Drawing Sheets

APPARATUS AND METHODS FOR UNIFORMLY DISTRIBUTING COOLANT WITHIN A CRYO-ABLATION DEVICE

RELATED APPLICATION DATA

The present application claims the benefit under 35 U.S.C. §119 of U.S. Provisional Application Ser. No. 61/029,825, filed on Feb. 19, 2008, the contents of which are incorporated herein by reference.

FIELD OF THE INVENTION

The present inventions relate to apparatus and methods for delivering coolant to a cryogenic ablation device and, more particularly, to apparatus and methods for uniformly distributing coolant within a cryo-ablation device.

BACKGROUND

Cardiac arrhythmias are a significant health problem, and atrial fibrillation is a common cardiac arrhythmia. Atrial arrhythmias may increase risk factors for various conditions such as embolisms and can contribute to the onset of ventricular arrhythmia.

It is believed that cardiac electrical impulses start in a sinoatrial (SA) node, spread through the atria, and progress through the atrial-ventricular (AV) node to the ventricles to complete a heartbeat. Atrial fibrillation is an irregular heart rhythm that originates in the atria or the upper two chambers of the heart. The pulmonary veins, in particular, can be sources of disruptive re-entrant electrical impulses.

One known manner of treating atrial fibrillation is by use of medication that is intended to maintain a normal sinus rate and/or decrease ventricular response rates. It is also known to use implant devices such as atrial pacemakers for this purpose. Further, other known methods and devices have been developed for creating therapeutic lesions, e.g., by minimally-invasive surgical methods, in the myocardial tissue to block unwanted electrical impulses that are believed to be the source of atrial fibrillation. In this context, ablation has come to mean the deactivation, or removal of function, rather than the actual removal of tissue. A number of energy sources may be used for creating these "blocking" lesions that are preferably transmural and extend across the entire heart wall.

Formation of lesions may be performed using both endocardial and epicardial devices and techniques. Endocardial procedures are performed from within the heart. Since the endocardium primarily controls myocardial functions, there are inherent advantages to generating lesions by applying an energy source to endocardial surfaces. One known manner of applying energy for this purpose is utilizing radio frequency (RF) catheters. Other known endocardial ablation devices include expandable balloons that are inflated with a cryogenic fluid or coolant, such as nitrous oxide. Examples of known lesion formation devices, including cryogenic balloon devices for use in endocardial ablation and their operation are described in U.S. Patent Application Publication No. 20060084962, U.S. Pat. Nos. 6,027,499; 6,468,297; 7,025,762; 7,081,112; 7,101,368 and 7,150,745, the contents of which are incorporated herein by reference.

For example, referring to FIG. 1, a system 100 for cryogenically ablating tissue utilizing a cryogenic balloon catheter 110 includes a source 120 of coolant or refrigerant 122 such as nitrous oxide or another suitable flowable coolant (generally referred to as coolant 122). During use, a cryogenic balloon catheter 110 is positioned within a desired location within a patient utilizing a guide wire 112 that extends through a guide wire tube, lumen or conduit 113. Coolant 122 is delivered through a console or an interface 130 and one or more connectors or tubes 140 to the balloon catheter 110 to inflate the expandable or balloon element 114 (generally referred to as balloon element 114) and cryogenically ablate adjacent tissue surrounding the chilled balloon element 114 or a portion thereof. Cryogenic cooling results from a pressure drop as the coolant 122 is sprayed into an inner space 116 defined by the balloon element 114, thereby causing the balloon element 114 to expand against and chill adjacent target tissue. During the procedure, the vacuum level within the balloon element 114 may be controlled using a vacuum source 150, and spent coolant 122 is evacuated from the balloon catheter 110 through the exhaust 160 or another suitable tube that may be a non-coaxial tube.

The effectiveness of balloon catheters 110 depends on various factors including, for example, the manner in which coolant 122 is distributed within the balloon element 114. More specifically, the effectiveness of chilling the balloon element 114 and cryo-ablation of adjacent tissue may depend on how uniform the temperature is along an inner surface 118 of the balloon element 114. Non-uniform temperatures may be caused by exposure to non-uniform or inconsistent or uneven coolant 122 flows, thereby resulting in temperature variations along the inner surface 118 and non-uniform chilling and cryo-ablation of tissue.

For example, referring to FIG. 2, a coil-shaped hypotube or coil 200 (a portion of which is illustrated) may be used to deliver and dispense coolant 122 to inflate the balloon element 114. FIG. 2 illustrates a portion of a coil-shaped hypotube 200 shaped to have an inner coil 210 and an outer coil 220 through which one or more straight apertures or holes 230 are drilled. Other straight apertures 230 (not shown in FIG. 2) may also be drilled through the outer coil 220. With this configuration, a radial line R extends from a central axis CA defined by the hypotube coil 200 and through the straight hole 210 such that the coolant 122 is dispersed perpendicularly 232 through the straight aperture 230 relative to an outer surface 222 of the outer coil 220 and into a space 242 defined between the outer coil 220 and the balloon element 114, thereby inflating the balloon element 114 and chilling and cryogenically ablating adjacent tissue.

As another example, referring to FIG. 3, other cryo-ablation devices may utilize a non-coiled tube 300 that also includes straight apertures 330a-d formed through the tube 300 such that coolant 122 is dispersed through the straight apertures 330 perpendicularly relative to the outer surface of the tube 300. The same flow characteristics described below may apply to both types of tubes 200, 300.

With the straight holes or apertures 230, 330 of known coolant delivery tubes 200, 300, coolant 122 is dispersed against the inner surface 118 of the balloon element 114 in an uneven manner. For example, with reference to FIGS. 3 and 4, as coolant 122 is dispersed through the straight apertures 330, the coolant 122 is initially concentrated at cold spots 410 to cool a section of the inner surface 118 of the balloon element 114, which also cools adjacent surfaces 412. However, initially, the temperature along the balloon inner surface 118 varies, e.g., sections 414 are warmer than the concentrated cold spots 410 and other cooled sections 412. For example, the temperature of a concentrated cold spot 410 may be about −80° C. whereas a temperature of a cooled section 412 may be about −20° C., and a temperature of a warmer section 414 may be about 0° C. to 37° C. Over time, this temperature differential may be reduced with continued cooling, but smaller temperature variations may still exist across the inner surface 118 of the balloon element 114, as shown in FIG. 5, thereby resulting non-uniform and non-uniform chilling and ablation of tissue. Further, while it may be possible to reduce these non-uniform cooling effects over time, doing may require longer procedures and larger quantities of coolant 122.

Further, known devices may require large amounts of coolant 122, a large number of nozzles and longer treatment times to compensate for uneven coolant distribution and cooling as shown in FIGS. 4-5. For example, large amounts of coolant 122 may be utilized to "overtreat" a tissue region, e.g., to form a cold spot 410 with the hope that passive conduction in the tissue will eventually migrate and fill in the space between a first tissue region or cold spot 410 and second tissue region or cold spot 410. For example, it has been demonstrated in experiments on animals that such passive conduction techniques may adequately fill a gap of about 6 mm between nozzles or between cold spots. However, certain known balloon elements 114 are about 23 mm in diameter and have a circumference of about 70 mm. Using nozzles that are spaced apart by about 6 mm (to achieve sufficient passive conduction), however, would require a minimum of 11-12 nozzles. Larger balloon elements 114, e.g., having a diameter of about 28 mm and an even larger circumference, would require even more nozzles. In these cases, larger quantities of coolant 122 are required, and such techniques require longer treatments to cool adjacent tissue regions.

Further, overpowering a balloon element 114 with additional coolant 122 may result in puddling or accumulation of liquid coolant 122 in the bottom of the balloon element 114. This accumulation of coolant 122 contributes to uneven treatment and may also pose safety risk if the catheter exhaust lumen becomes plugged or the balloon element 114 ruptures since 1 cc of liquid coolant may evaporate into about 700 cc of gas.

SUMMARY

According to one embodiment, an apparatus, e.g., in the form of a nozzle, for uniformly distributing or dispersing coolant within a cryo-ablation device includes a tubular member or conduit, which may be a straight tubular member, having inner and outer surfaces, proximal and distal ends, defines a lumen and a plurality of angled apertures. A coolant or refrigerant may flow through the lumen and through the angled apertures.

According to another embodiment, an inflatable cryo-ablation apparatus includes an inflatable element, such as a balloon, having inner and outer surfaces and defining an inner space, and a tubular member. The tubular member is in fluid communication with the inner space of the first inflatable element. The tubular member includes inner and outer surfaces and a lumen through which coolant flows to the inner space of the inflatable element. The tubular member defines a plurality of angled apertures through which cooling can flow.

A further embodiment is directed to a method of uniformly distributing coolant within a cryo-ablation device. The method includes delivering a coolant though a tubular member that is positioned within the cryo-ablation device and dispersing streams of coolant from apertures formed in the tubular member. The tubular member includes inner and outer surfaces, proximal and distal ends, and a lumen through which coolant is delivered to apertures. Coolant is dispersed from the tubular member lumen and through the angled apertures.

Yet another embodiment is directed to a method of inflating a cryo-ablation device and includes delivering a coolant though a tubular member positioned within the cryo-ablation device. The tubular member has inner and outer surfaces, and a lumen through which coolant flows. The method further includes dispersing a plurality of streams of coolant from the tubular member through respective angled apertures, around the outer surface, and along an inner surface of a first inflatable element.

In one or more embodiments, a tubular member or nozzle is configured such that streams of coolant dispersed from tubular member through the plurality of angled apertures initiate swirling of coolant streams around the outer surface of the tubular member. Further, in one or more embodiments, coolant streams dispersed through angled apertures are uniformly distributed along a surface of the cryo-ablation device, e.g., in a substantially annular band within the cryo-ablation device.

In one or more embodiments, the tubular member may be a hypotube and may have a coil shape. The tubular member may also be plastic and may be linear rather than a coil shape.

Further, in one or more embodiments, the tubular member may include about four to about ten angled apertures, and each angled aperture may define an axis. The tubular body also defines a central axis. A line extending radially from the central axis to the angled aperture defines an acute angle between the axis of the angled aperture and the line extending radially from the central axis. The axis of the aperture lines in a plane that is normal to the central axis of the tubular member. The apertures are arranged to have a common inclination such that coolant flowing through the apertures flows in the same direction, e.g., clockwise or counter-clockwise. The acute angle may be about 10 degrees to about 75 degrees and may be sufficiently large such that the aperture has a sufficiently large horizontal component and no line extending radially from the central axis of the tubular member extends completely through an angled aperture.

In one or more embodiments, angled apertures are evenly spaced around the tubular member, i.e. they are equidistant from each other. In another embodiment, apertures are unevenly spaced around the tubular member. Uneven aperture spacing may be useful to compensate for pressure differences in the tubular member. Angled apertures may be defined at one location along a length of the tubular member or at multiple locations along the length of the tubular member.

Further, in one or more embodiments, each angled aperture has a width of about 0.003", a length of about 0.003", and extends through the tubular member having a thickness of about 0.003" to about 0.030".

Additionally, in one or more embodiments, streams of coolant, such as nitrous oxide, flowing through the angled apertures flow in the same direction (e.g., all counter-clockwise or all clockwise) and swirl and circulate along an inner surface of an inflatable member such as a balloon. This forms a swirling flow of coolant that exposes a circumferential annular section of the inner surface of the first inflatable element to substantially similar quantities of coolant, thus providing a cooling temperature that is substantially constant along the annular inner surface, thereby providing for uniform ablation of a desired annular ring of tissue.

In one or more embodiments, a cryo-ablation apparatus includes two inflatable elements. The tubular member and a first inflatable element are configured such that streams of coolant dispersed through the plurality of apertures of the tubular member swirl around the tubular member and along the inner surface of the inflatable element to inflate the first inflatable element and the second inflatable element.

In one or more embodiments, a tubular member including angled apertures may be a component of a system that also includes an inner tube disposed within the tubular member that delivers coolant to the tubular member coolant, which is then dispersed through the angled apertures to an inner space defined by an inflatable element. Spent coolant may then be exhausted through an inner space defined between the tubular member and the inflatable element by a spacer element.

BRIEF DESCRIPTION OF THE DRAWINGS

Referring now to the drawings in which like reference numbers represent corresponding parts throughout and in which.

DETAILED DESCRIPTION OF ILLUSTRATED EMBODIMENTS

Embodiments relate to apparatus and methods for inducing coolant to swirl around a tubular member when dispersed from the tubular member such that dispersed coolant swirls or circulates along an inner surface of a balloon element. In this manner, embodiments provide for uniform or substantially uniform coolant distribution in an annular band along the inner surface of a balloon element. In this manner, a temperature along the inner surface of the balloon element is substantially constant and the substantially constant temperature can be achieved more quickly compared to known devices, which may require more time and coolant in order to achieve a desired temperature and temperature distribution along the balloon element inner surface to compensate for initial temperature differential resulting from dispersing coolant through straight apertures. The distribution and swirling of coolant achieved with embodiments results in uniform or substantially uniform ablation of tissue adjacent to or around the balloon element. Various embodiments and aspects thereof are described in further detail with reference to FIGS. 6-16.

Figure 1:
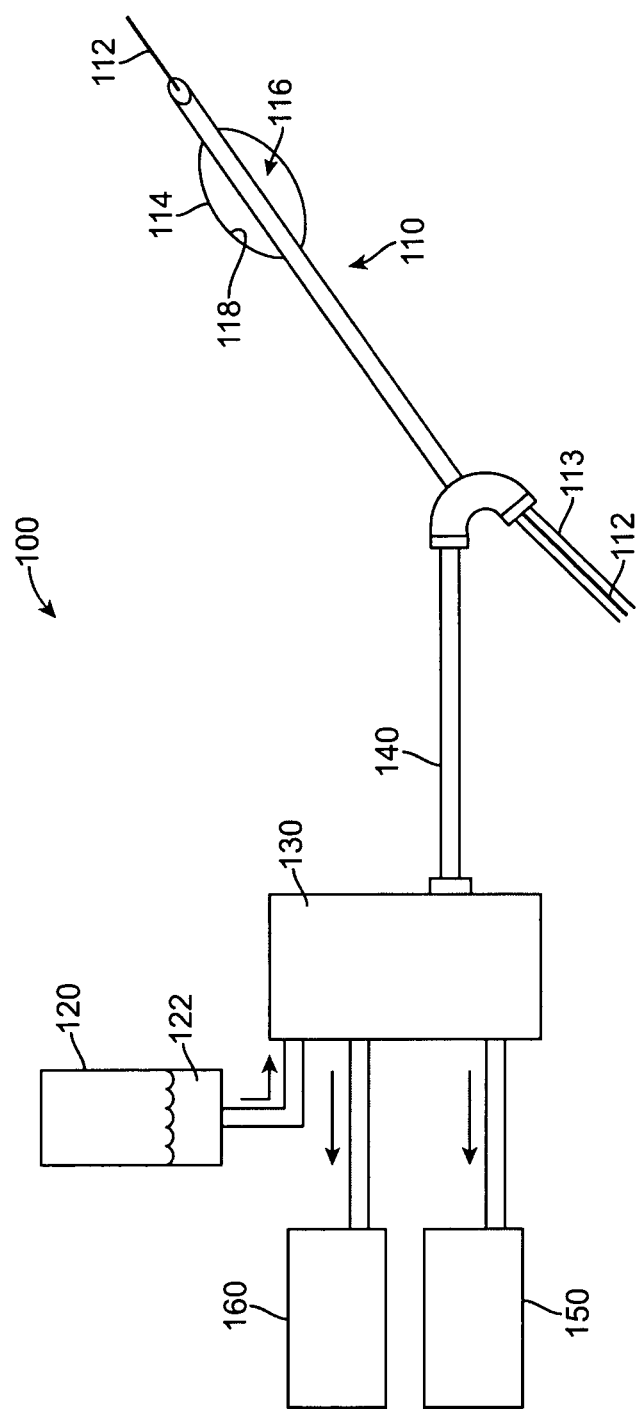
FIG. 1 schematically illustrates components of a known cryo-ablation system including a cryogenic ablation catheter.
Figure 2:
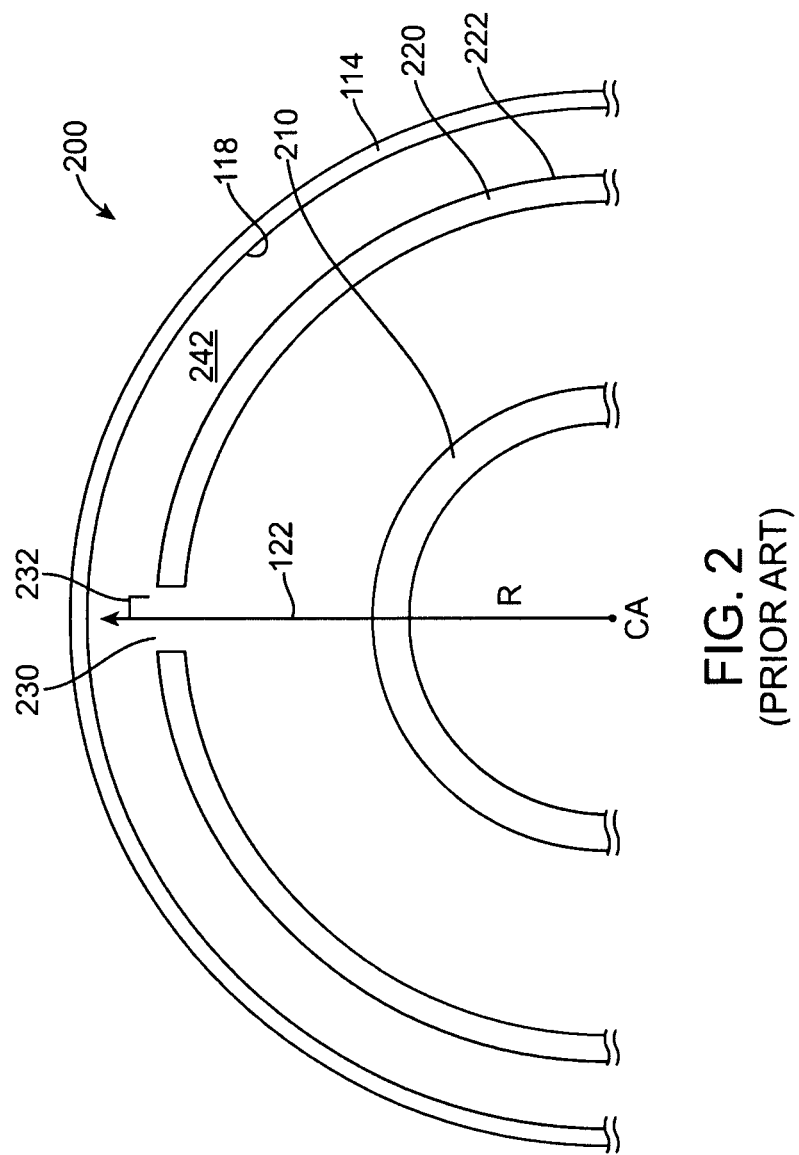
FIG. 2 is a partial cross-sectional view of a known coil-shaped hypotube including straight apertures or holes for use in the system shown in FIG. 1.
Figure 6:
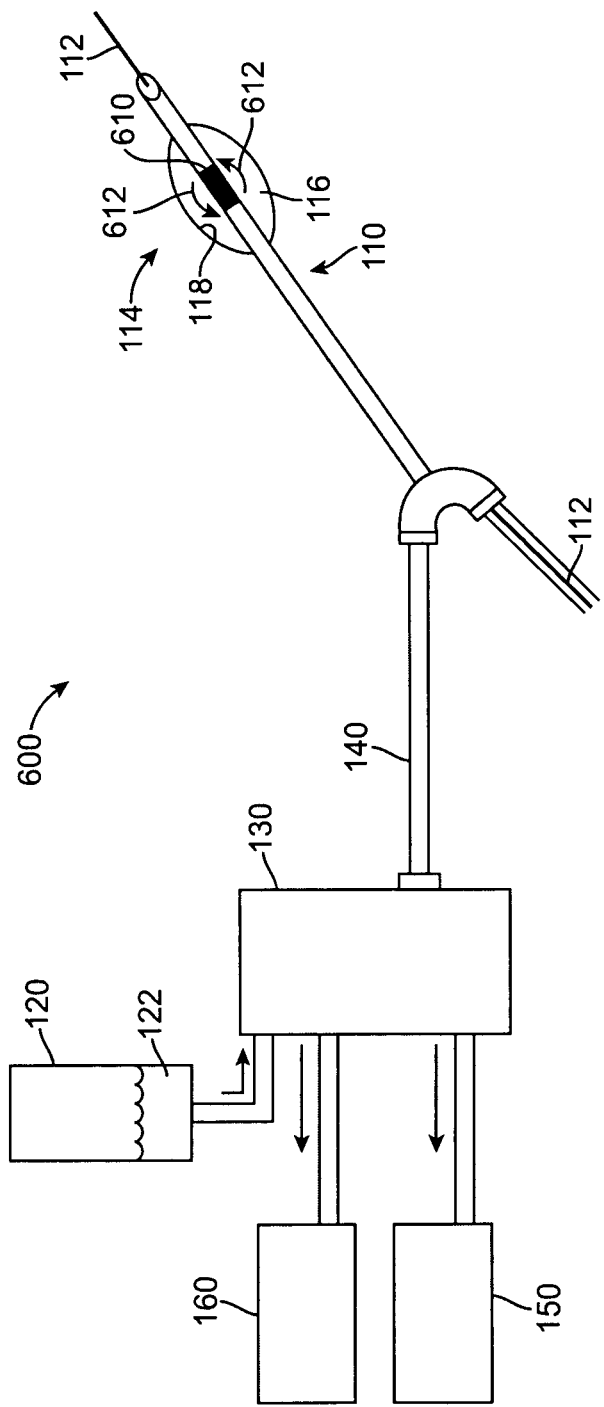
FIG. 6 illustrates a cryo-ablation system including a cryogenic balloon catheter that includes a swirl inducing or canted nozzle apparatus constructed according to one embodiment.

Referring to FIG. 6, a cryogenic ablation system 600 constructed according to one embodiment includes a swirl inducing or canted nozzle apparatus 610 (generally referred to as nozzle 610) that is configured for dispersing and circulating coolant or refrigerant 122 within a cryo-ablation device, such as a balloon catheter 110, and may include certain other components as shown in FIG. 1. One suitable coolant 122 that may be utilized with embodiments is nitrous oxide, which may be a liquid, a gas or a mixture of a liquid or gas. Other coolants 122 may also be utilized including, for example, $CO_2$, Ar, $N_2$ and Freon. For ease of explanation, reference is made to a coolant 122 generally, one example of which is nitrous oxide, but it should be understood that other coolants 122 may be used with embodiments.

Figure 4:
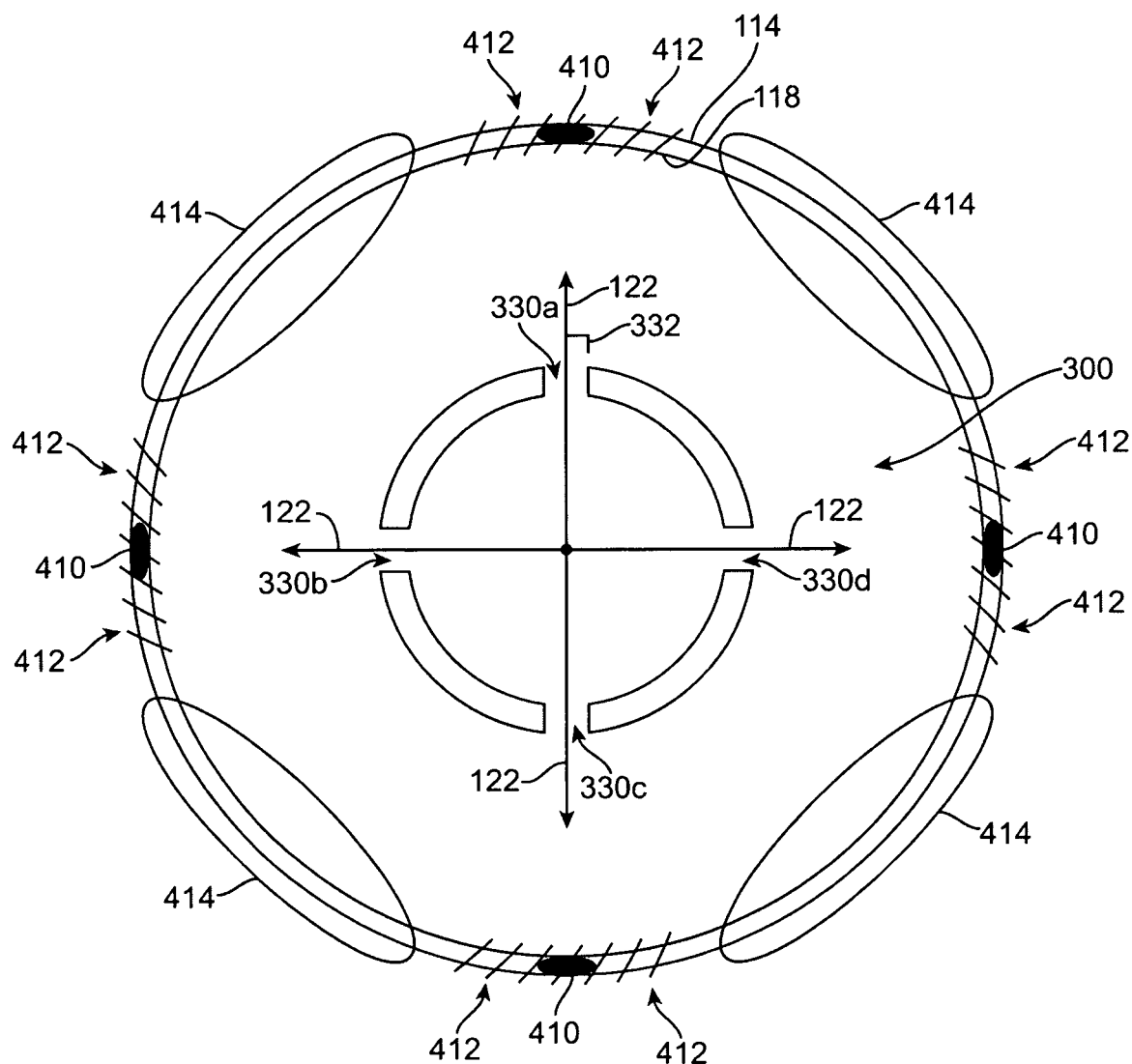
FIG. 4 illustrates temperature variations along an inner surface of a balloon element resulting from flow of coolant through straight apertures of known coolant delivery devices.
Figure 5:
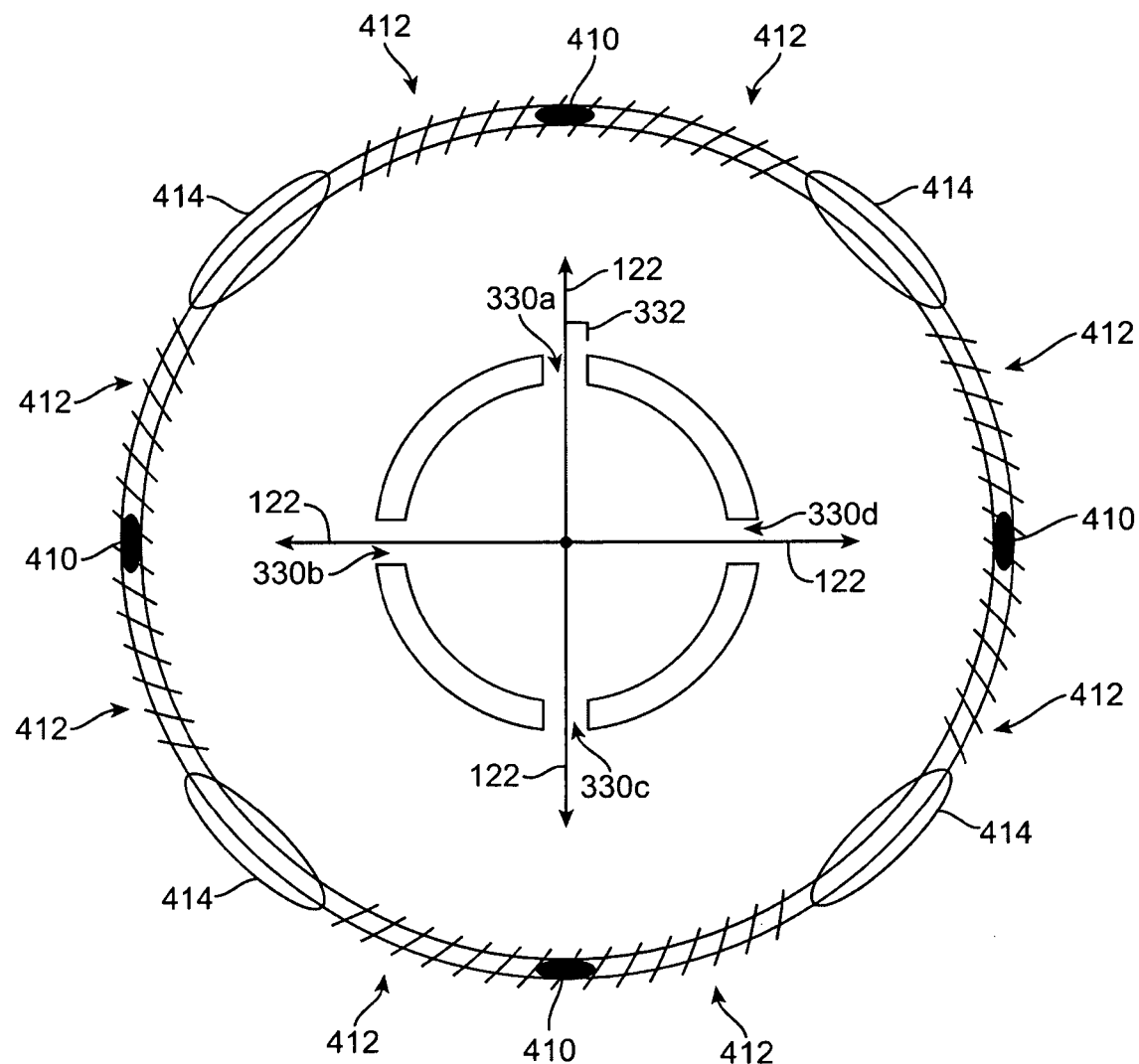
FIG. 5 further illustrates temperature variations along an inner surface of a balloon element resulting from flow of coolant through straight apertures of known coolant delivery devices.

As generally illustrated in FIG. 6, the nozzle 600 is configured such that coolant 122 that is dispersed from the nozzle 600 swirls 612 around the nozzle 610 to uniformly distribute coolant 212 in an annular band along the inner surface 118 of the balloon element 114. With this structure, embodiments are able to reduce or eliminate temperature differentials that would otherwise result when using known devices (as generally illustrated in FIGS. 4-5). As a result, with embodiments, the temperature along the annular inner surface 118 is substantially constant due to the uniform or substantially uniform distribution and spiral flow 612 of coolant 212, thereby providing uniform or substantially uniform cryo-ablation of tissue that is adjacent to or that surrounds the balloon element 114.

Figure 7:
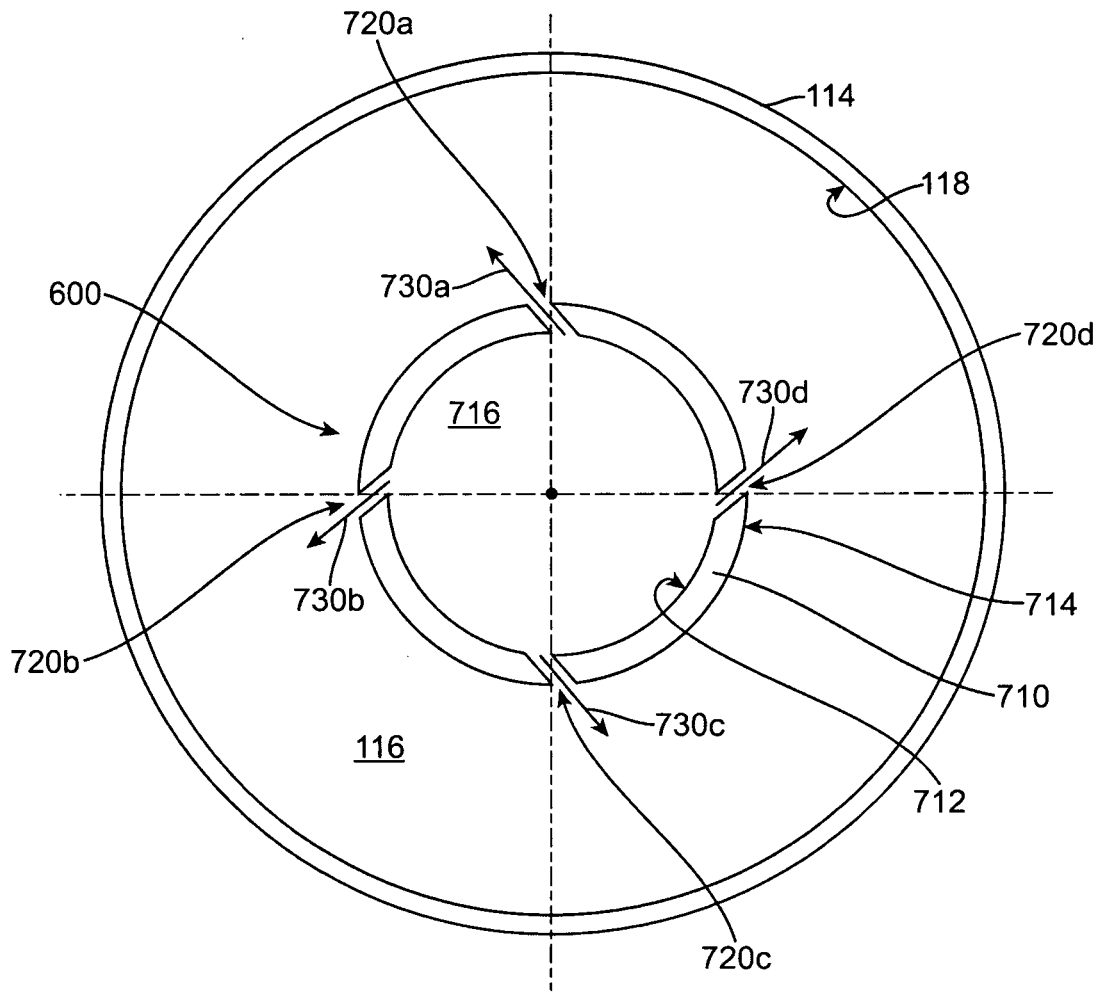
FIG. 7 is a cross-sectional view of a swirl inducing or canted nozzle apparatus constructed according to one embodiment and disposed within a balloon element and illustrating release of coolant through angled apertures.

Referring to FIG. 7, a swirl inducing or canted nozzle 600 constructed according to one embodiment includes a conduit or tubular member 710 (generally referred to as tubular member 710) having an inner surface 712 and an outer surface 714. The inner surface 712 defines a lumen 716 through which coolant 122 flows. The tubular member 710 may be plastic, metal (e.g., hypotube) or another suitable material. According to embodiments, the tubular member 710 defines a plurality of angled apertures 720.

In one embodiment in which the tubular member 710 is plastic, angled apertures 720 may be formed through the tubular member 710 by heating the plastic and pushing a wire or other suitable device through the tubular member 710 to form an angled aperture 720. This embodiment may be particularly suitable in application in which drilling through a hypotube is not cost effective or if drilling apertures at correct locations and angles along a curved surface of the coil presents difficulties.

In the illustrated embodiment, the tubular member 710 defines four angled apertures 720a-d (generally referred to as angled apertures 720). According to one embodiment, the apertures 720 have a common inclination and are configured such that streams 730a-d of coolant 122 (generally referred to as streams 730) are dispersed through the angled apertures 720 and into the space 116 defined between the outer surface 714 of the tubular member 710 and the inner surface 118 of the balloon element 114. In the illustrated embodiment, the apertures 720 are arranged such that the streams 730 swirl in the same direction to induce or form an initial spiral coolant flow pattern. In the illustrated embodiment, the common aperture 720 inclination results in initiation of coolant spiraling in a counter-clockwise direction, but in other embodiments, coolant streams 730 may flow in a clockwise direction if the apertures 720 are angled in an opposite direction.

Figure 8:
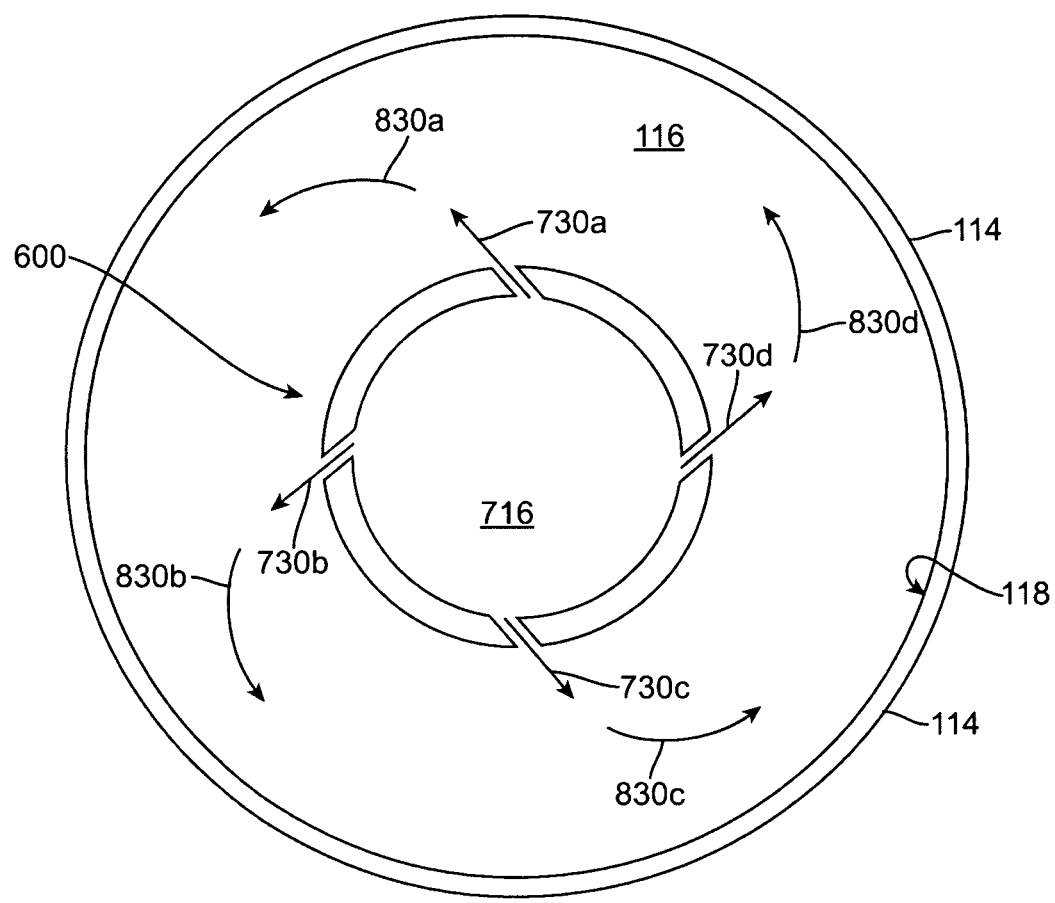
FIG. 8 illustrates release of additional coolant through angled apertures of the nozzle apparatus shown in FIG. 7 and resulting spiral coolant flows.

Referring to FIG. 8, coolant 122 is supplied by the coolant source 120 and flows through the lumen 716 of the tubular member 710. The coolant 122 is dispersed through the angled apertures 720, and the initial streams 730 (shown in FIG. 7) are enhanced, grow and/or gain momentum to form more pronounced coolant streams 830a-d (generally 830). These more pronounced coolant streams 830 begin to circulate within the space 116 defined between the tubular member 710 and the balloon element 114.

Figure 9:
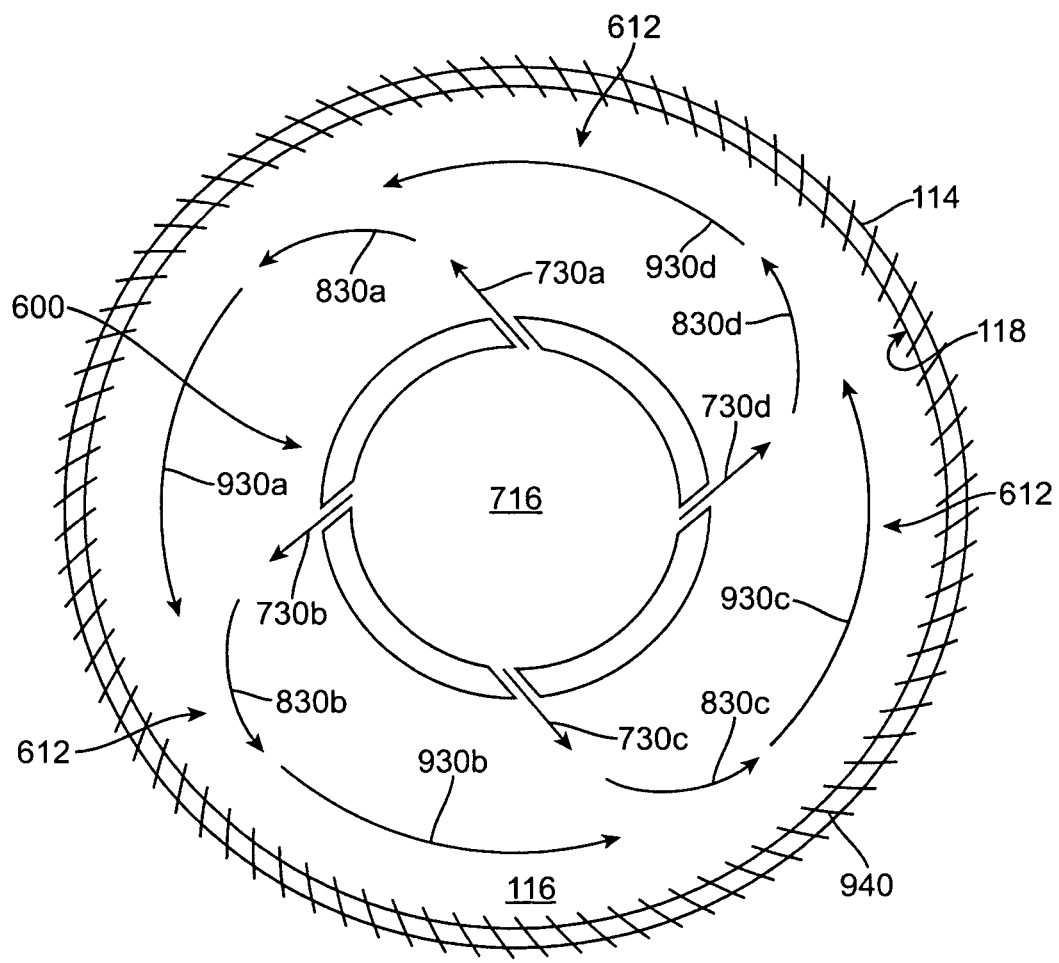
FIG. 9 illustrates spiral coolant flows merging and developing into a uniform flow of coolant that circulates along an inner surface of a balloon element and resulting uniform temperatures along the balloon element inner surface.

Referring to FIG. 9, as coolant 122 continues to flow through the angled apertures 720, the initial streams 830 are enhanced, grow and/or gain further momentum to develop into even more pronounced streams 930a-d that merge or combine into a uniform flow of coolant 612 that circulates within the space 116 along the inner surface 118 of the balloon element 114. In this manner, coolant 122 is uniformly distributed along a circumferential section of the inner surface 118 to provide a uniform or substantially uniform temperature 940 across the inner surface 118 (as generally illustrated by hash marks around the balloon element 114. Thus, with embodiments, there are no coolant concentrations or cold spots 410 and warmer regions 414 (as shown in FIGS. 4 and 5), thus allowing for uniform ablation of tissue adjacent to the balloon element 114.

Figure 10:
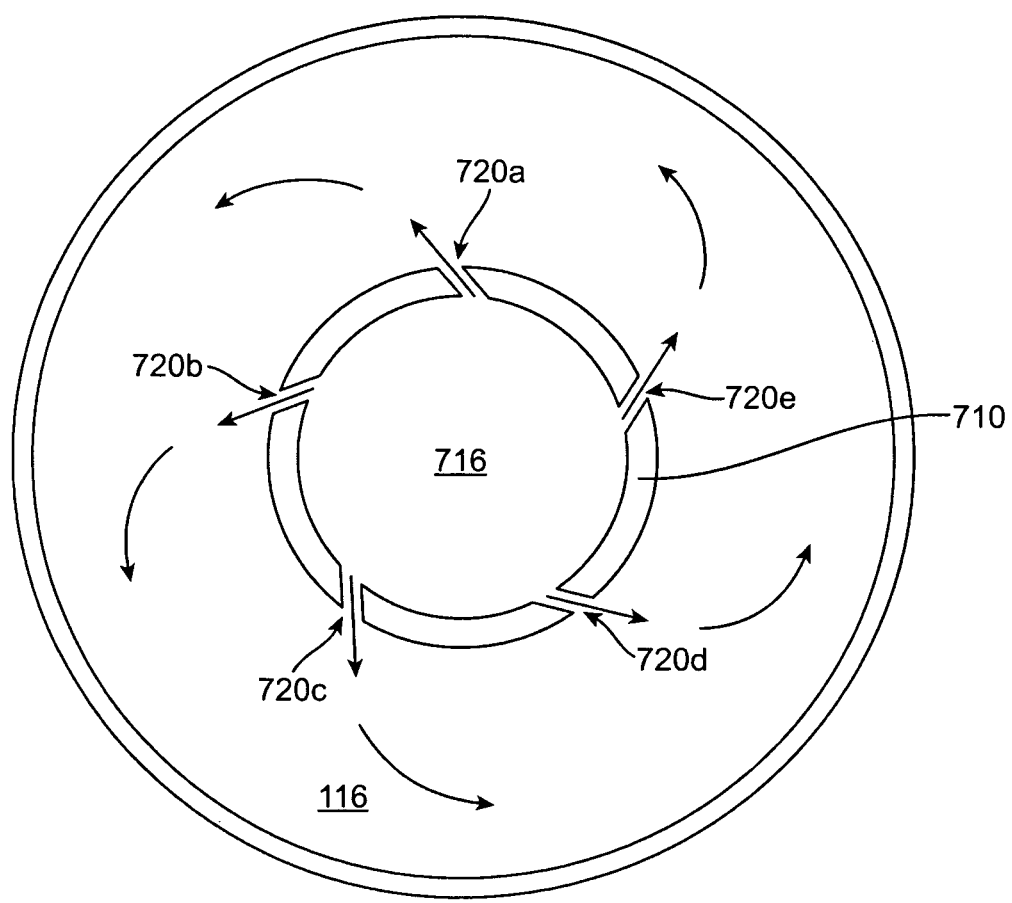
FIG. 10 is a cross-sectional view of a swirl inducing or canted nozzle apparatus constructed according to another embodiment and including five angled apertures.
Figure 11:
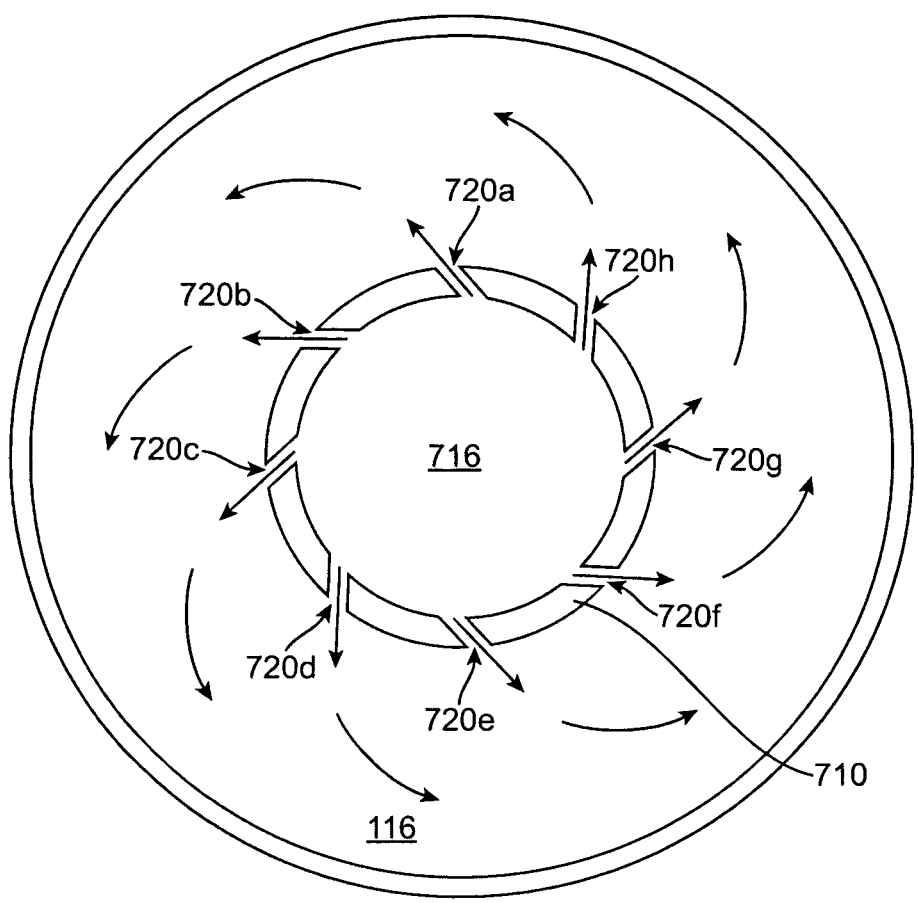
FIG. 11 is a cross-sectional view of a swirl inducing or canted nozzle apparatus constructed according to another embodiment and including eight angled apertures.

Although FIGS. 7-9 illustrate a tubular member 600 defining four angled apertures 720a-d, other swirl inducing or canted nozzle 600 embodiments may include different numbers of angled apertures 720 while inducing spiral coolant flows to achieve constant or substantially constant temperatures 940 across a balloon element 114. For example, in other embodiments, a tubular member 710 may define three angled apertures 720a-c; five angled apertures 720a-e (as shown in FIG. 10), and larger numbers of angled apertures 720, e.g., eight angled apertures 720a-h (as shown in FIG. 11). FIGS. 7-11 are provided as examples of how embodiments may be implemented and to demonstrate that a tubular member 710 may include various numbers of angled apertures 720 to induce spiral coolant flows. Further, it should be understood that the number and configuration of angled apertures 720 may depending on various operating parameters including one or more of the size and configuration of the tubular member 710, the size and configuration of the angled apertures 720, the coolant 122 pressure, the flow rate of coolant 122 through the lumen 716, and the flow rate of coolant streams 730 through the angled apertures 720.

Figure 12:
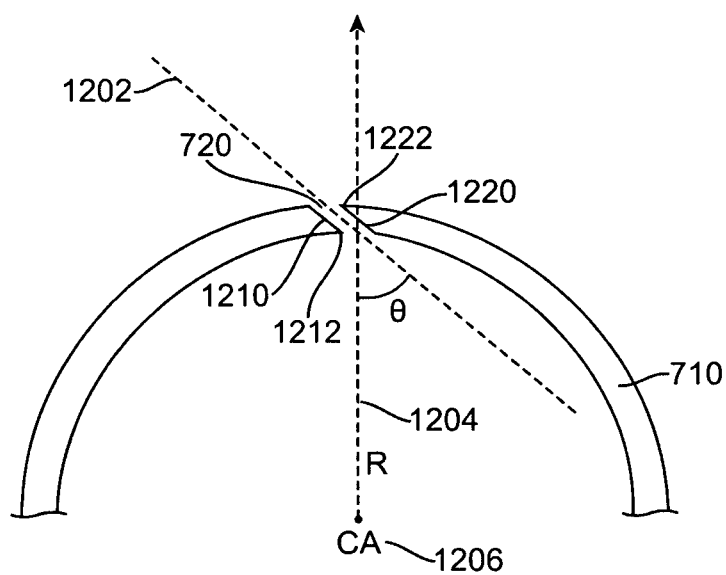
FIG. 12 illustrates an angular configuration of an angled aperture of a swirl inducing or canted nozzle apparatus constructed according to one embodiment.

Referring to FIG. 12, in one embodiment, an angled aperture 720 defines an axis 1202. A radial line 1204 extends from a central axis 1206 of the tubular member 710 and through the aperture 720. In the illustrated embodiment, an acute angle (θ) is defined between the axis 1202 and the radial line 1204. According to one embodiment, the acute angle (θ) is about 10 to about 75 degrees, e.g. about 45 degrees. In one embodiment, all of the angled apertures 720 are configured in the same manner such that each angled aperture 720 defines the same acute angle (θ) defined by respective axes 1202 and radial lines 1204.

Figure 3:
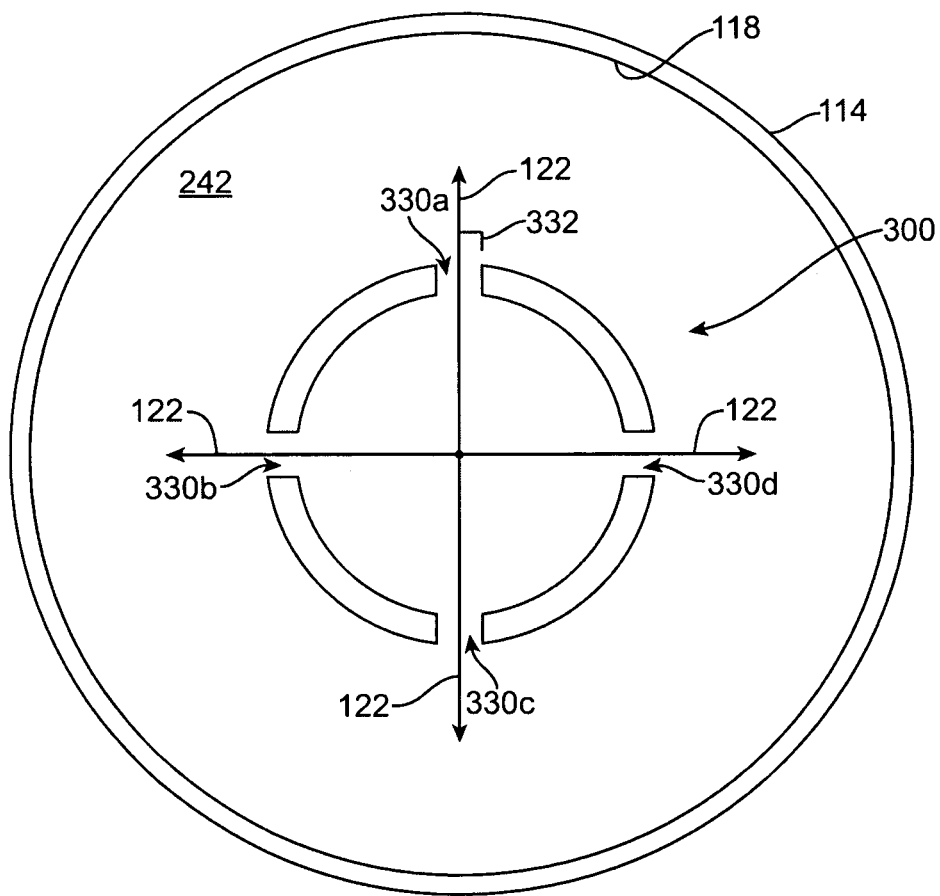
FIG. 3 is a cross-sectional view of a known coolant delivery tube including straight apertures or holes and disposed within a balloon element.

In the illustrated embodiment, an angled aperture 720 is defined by and between a first edge 1210 of the tubular member 710 having an inner pointed end 1212 and a second edge 1220 of the tubular member having an outer pointed end 1222. Thus, an angled aperture 720 is not a straight aperture as shown in FIG. 3-5 or as in known devices. In one embodiment, as illustrated in FIG. 12 the acute angle (θ) is sufficiently large such that no radial line 1204 that extends from the central axis 1206 extends completely through an angled aperture 720. Rather, as shown in FIG. 12, for example, the angled aperture 720 has a shape and size such that a portion of the pointed tip 1222 of the tubular member is within the path of the radial line 1204. This is in contrast to straight aperture 330 devices as shown in FIGS. 3-5, in which a radial line extends straight through the straight aperture 330.

One manner of forming the angled apertures 720 is to pierce the wall of the tubular member 710 using a piercing rod, wire or other suitable device. For this purpose, the tubular member 710 wall may be made of a soft material that can be pierced or made to be deformable such that the piercing rod may extend through the wall of the tubular member 710, thereby forming an initial linear aperture. The piercing rod may then be moved within the initial linear aperture in a lever-type or back-and-forth action to change the shape and/or direction of the aperture and form an angled aperture 720. This process may result in a dimple-like structure defining an angled aperture 720.

More particularly, due to the lever-type motion, one surface, e.g., the first edge 1210, may be pushed inwardly or downwardly, whereas another surface, e.g., the second edge 1220, may be levered or pushed outwardly or upwardly. Thus, one edge 1210 is low and one edge 1220 is high, thereby forming a dimple-like structure that defines an angled aperture 720. It should be understood that angled apertures 720 may be formed using different methods, and that this method is provided as an example of how embodiments may be implemented.

It should also be understood that the particular configuration of angled apertures 720 may depend on or more factors, e.g., one or more of the number of angled apertures 720, the thickness of the tubular member 710, the width of the angled aperture 710, and the manner in which the angled apertures 720 are formed. In one embodiment, a plastic tubular member 710 has an outer diameter of about 0.040", an inner diameter of about 0.030", a thickness of about 0.005", and includes about five angled apertures 720. In one embodiment, each angled aperture 720 has a width or diameter of about 0.003" and forms an acute angle (as shown in FIG. 12) of about 45 degrees.

Figure 13:
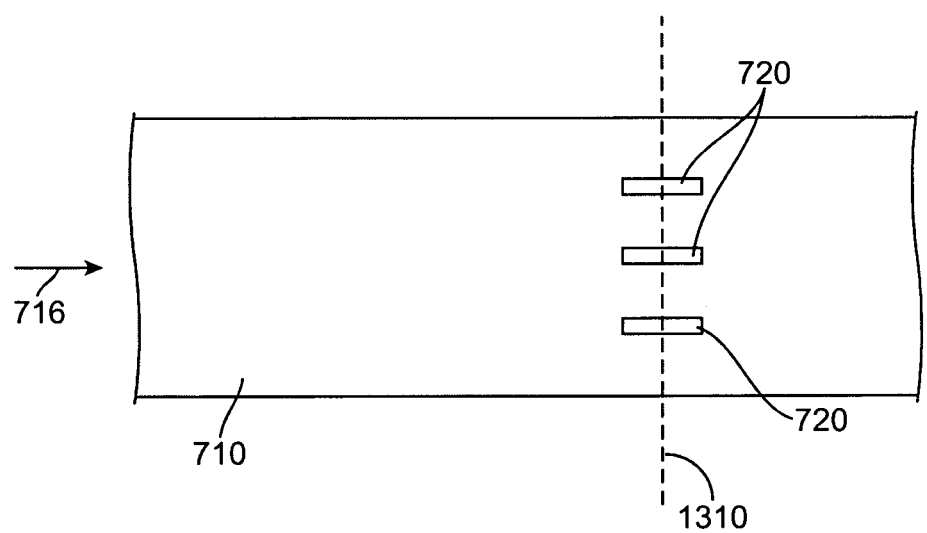
FIG. 13 is a partial side view of a swirl inducing or canted nozzle apparatus including angled apertures formed through a single location along a length of the nozzle apparatus.
Figure 14:
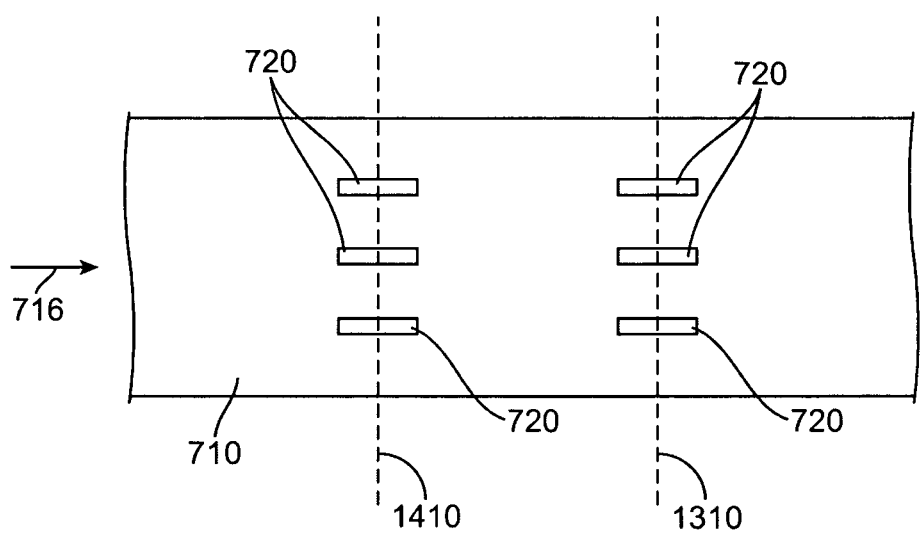
FIG. 14 is a partial side view of a swirl inducting or canted nozzle apparatus including angled apertures formed through a multiple locations along a length of the nozzle apparatus.
Figure 15:
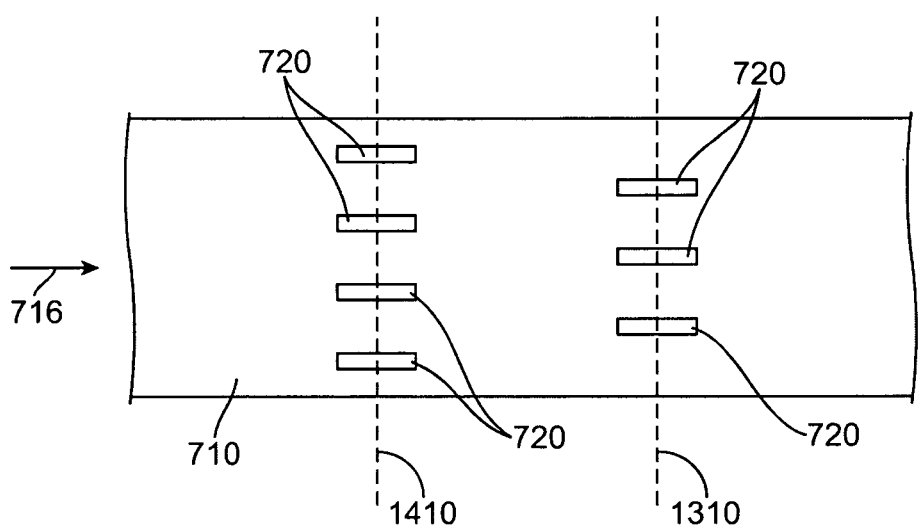
FIG. 15 is a partial side view of a swirl inducting or canted nozzle apparatus including angled apertures formed through a single location along a length of the nozzle apparatus and different numbers of angled apertures at different locations along the length of the nozzle apparatus.

Further, as shown in FIGS. 13-15, embodiments may include angled apertures 720 that are located along various sections of a tubular member 710. For example, referring to FIG. 13, in one embodiment, all of the angled apertures 720 are defined at one location along a length of the tubular member 710. In other embodiments, the angled apertures 720 are defined at different locations along the length of the tubular member 710. In other words, the angled apertures 720 may be formed within a single cross-sectional plane 1310 as shown in FIG. 13 or within multiple cross-sectional planes 1310, 1410 as shown I FIG. 14. Further, the number of angled apertures 720 at each location or within each plane 1310, 1410 may be the same (as shown in FIG. 14) or different (as shown in FIG. 15).

Figure 16:
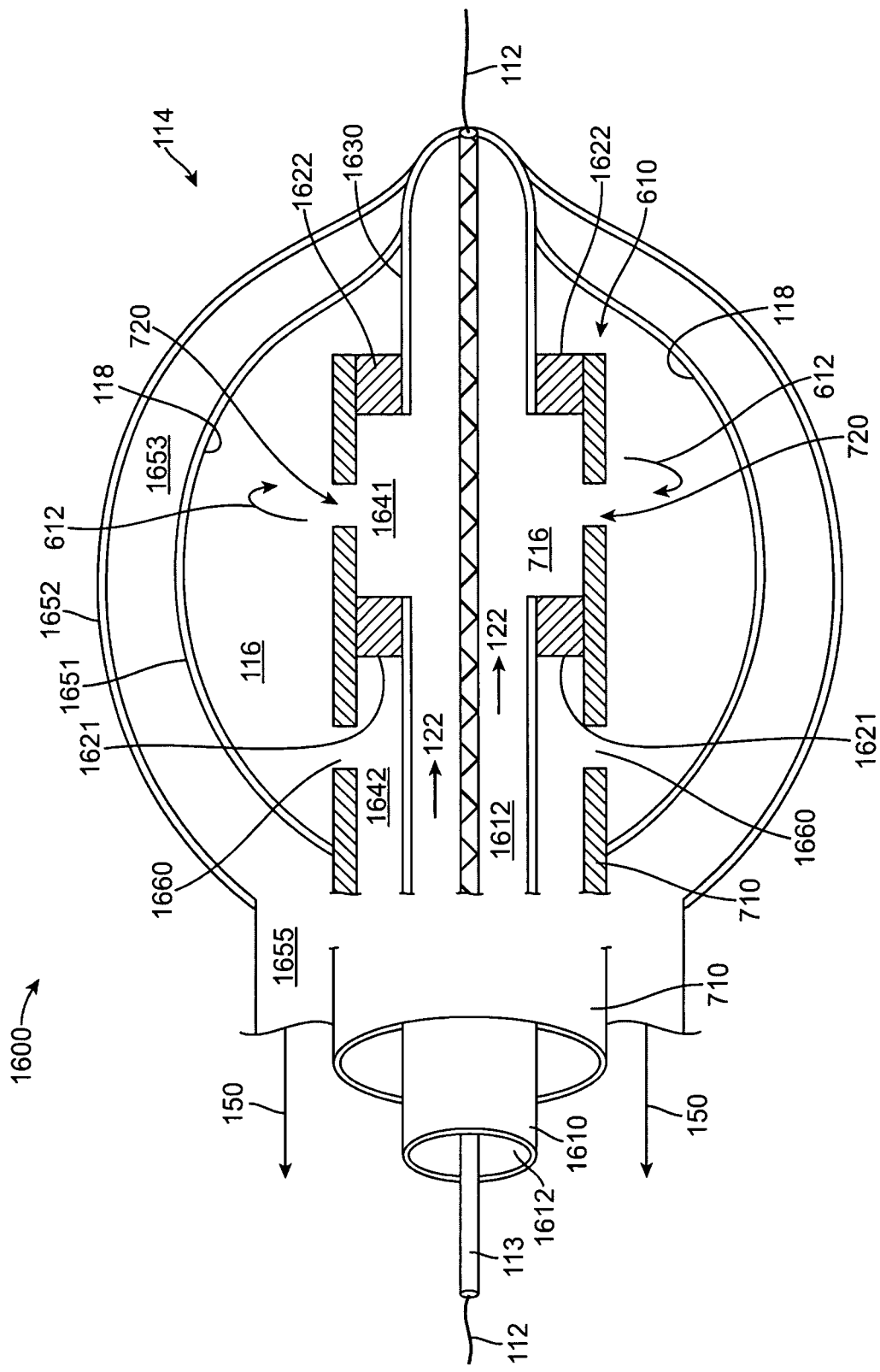
FIG. 16 illustrates another system in which swirl inducing or canted nozzle apparatus embodiments may be implemented.

Having described different embodiments of a swirl inducing or canted nozzle 600, following is a more detailed description of a cryo-ablation device that may include nozzle 600 embodiments. FIG. 16 generally illustrates one such system 1600 in which nozzle 610 embodiments may be utilized to achieve uniform spiral flows 612 to uniformly distribute coolant 122 in an annular band along an inner surface 118 of a cryogenic balloon catheter 110. It should be understood, however, that nozzle 600 embodiments may be implemented in various other cryogenic ablation systems.

In the illustrated embodiment, a system 1600 includes a spiral inducing or canted nozzle 610 that is a part of a co-axial cryo-ablation device. The nozzle 610 having angled apertures 720 forms an outer or first tubular member 710 defining a lumen 716, and an inner or second tubular member 1610 is disposed within the lumen 716 and is in fluid communication with the lumen 716. Coolant 122 supplied by a source 120 flows through a lumen 1612 of the inner member tubular member 1610 and into the lumen 716 of the tubular member 710.

In the illustrated embodiment, the inner tubular member 1610, terminates within the lumen 716 and is separated from the tubular member 710 by a first spacer 1621, e.g., an annular spacer. Another portion of the inner tubular member 1610, or a cap member 1630 forms the distal end and cap of the cryo-ablation device and is separated from the outer tubular member 710 by a second space 1622, e.g., an annular spacer. This configuration defines a first inner space 1641 within the tubular member 710 and a second inner space 1642

During use, coolant 122 flows from the inner tubular member 1610 and into the first inner space 1641, and is then dispersed through angled apertures 720 of a canted nozzle constructed according to embodiments. The outer tubular member 710 may be movable, e.g., rotatable, by a user to adjust the direction of coolant 122 that is dispersed through the angled apertures 720. In an alternative embodiment, a sleeve (not shown in FIG. 16) may be positioned over the outer surface of the tubular member 710 and may be moved to allow a user to selectively block or open certain angled apertures 720.

The coolant streams 730/830 result in coolant swirling 612 within the space 116 defined between a first expandable element 1651, such as a balloon element, and the outer tubular member 710. The swirling coolant 612 expands or inflates the expandable element 1651 which, in turn, expands or inflates a second expandable element 1652, such as a balloon. Spent coolant is exhausted from the inner space 116 through apertures 1660 (which may be straight apertures rather than angled apertures 720) into the second inner space 1642 such that the spent coolant can be exhausted from the outer tubular member 710. The vacuum level in the space 1653 between the first and second expandable elements 1651, 1652 may be controlled using a vacuum source 150 and a vacuum lumen 1655 (generally and partially illustrated in FIG. 16).

Although particular embodiments have been shown and described, it should be understood that the above discussion is not intended to limit the scope of these embodiments. Various changes and modifications may be made without departing from the scope of the claims.

For example, swirl inducing or canted nozzle embodiments may be implemented using tubular members having various shapes, including coil-shaped tubular members and linear tubular members. The tubular member may include a single tube or have a multi-tube or co-axial arrangement. Further, nozzle embodiments may be implemented using tubular members of different materials, including plastic and hypotube materials. Nozzle embodiments may also be used with various cryogenic ablation systems.

Further, embodiments may be configured to perform ablation of various types of tissue for treatment of different conditions or diseases, one example of which is to perform endocardial ablation to treat atrial fibrillation. Moreover, although embodiments are described with reference to a nitrous oxide coolant, embodiments may be used to disperse other types of coolant, and the coolant may be gaseous and/or liquid when dispersed. Thus, embodiments are intended to cover alternatives, modifications, and equivalents that may fall within the scope of the claims.

What is claimed is:

1. A nozzle apparatus for distributing coolant within a cryo-ablation device, comprising:
a tubular member having substantially straight, parallel walls defined by an inner surface and an outer surface, the inner surface defining a lumen through which coolant may flow, the tubular member defining a plurality of angled apertures extending between the inner and outer surfaces of the walls such that coolant flowing through the lumen is dispersed from the tubular member through the plurality of apertures and into a space defined by the cryo-ablation device, wherein the tubular member includes an outer tubular member and an inner tubular member, the inner tubular member disposed within and spaced apart from the outer tubular member, the inner tubular member defining a lumen in fluid communication with a lumen of the outer tubular member, the outer tubular member defining the plurality of angled apertures, the outer tubular member further defining a second plurality of apertures, wherein the outer and inner tubular members are configured such that coolant flows through the lumen of the inner tubular member, into the lumen of the outer tubular member, and out through the plurality of angled apertures, wherein spent coolant may be returned through the second plurality of apertures into a space between the outer and inner tubular members.

2. The nozzle apparatus of claim 1, the tubular member being configured to initiate swirling of streams of coolant dispersed from the tubular member through the respective plurality of angled apertures.

3. The nozzle apparatus of claim 1, the tubular member being configured to uniformly distribute coolant within a substantially annular band within the cryo-ablation device.

4. The nozzle apparatus of claim 1, wherein the tubular member is coil-shaped.

5. The nozzle apparatus of claim 1, each angled aperture defining an axis and the tubular member defining a central axis, wherein an acute angle of about 10 degrees to about 75 degrees is defined between an axis defined by an angled aperture and a line extending radially from the central axis to the angled aperture.

6. The nozzle apparatus of claim 5, the acute angle being sufficiently large such that no line extending radially from the central axis of the tubular member to an angled aperture extends completely through the angled aperture.

7. The nozzle apparatus of claim 1, the tubular member defining about four to about ten angled apertures.

8. The nozzle apparatus of claim 1, the plurality of angled apertures having a common inclination such that streams of coolant dispersed from the tubular member through the plurality of angled apertures swirl around the outer surface of the tubular member in the same direction.

9. An inflatable cryo-ablation apparatus, comprising:
a first inflatable element having an inner surface and an outer surface, the inner surface defining an inner space; and
a tubular member having substantially straight, parallel walls defined by an inner surface and an outer surface, the inner surface of the tubular member defining a lumen through which coolant may flow, the tubular member defining a plurality of angled apertures extending between the inner and outer surfaces of the walls such that coolant flowing through the lumen is dispersed from the tubular member through the plurality of apertures and into the inner spaced defined by the first inflatable element, wherein the tubular member includes an outer tubular member and an inner tubular member, the inner tubular member disposed within and spaced apart from the outer tubular member, the inner tubular member defining a lumen in fluid communication with a lumen of the outer tubular member, the outer tubular member defining the plurality of angled apertures, the outer tubular member further defining a second plurality of apertures, wherein the outer and inner tubular members are configured such that coolant flows through the lumen of the inner tubular member, into the lumen of the outer tubular member, and out through the plurality of angled apertures into the inner space of the first inflatable element, wherein spent coolant may be exhausted through the second plurality of apertures into a space between the outer and inner tubular members.

10. The inflatable cryo-ablation apparatus of claim 9, the tubular member being configured to initiate swirling of streams of coolant dispersed from the tubular member through the plurality of angled apertures and in the inner space defined by the first inflatable element.

11. The inflatable cryo-ablation apparatus of claim 9, the tubular member being configured to uniformly distribute coolant within a substantially annular band within the first inflatable element.

12. The inflatable cryo-ablation apparatus of claim 9, wherein the tubular member is a coil-shaped.

13. The inflatable cryo-ablation apparatus of claim 9, each angled aperture defining an axis and the tubular member defining a central axis, wherein an acute angle is defined between an axis defined by an angled aperture and a line extending radially from the central axis to the angled aperture.

14. The inflatable cryo-ablation apparatus of claim 13, wherein the acute angle is about 10 to about 75 degrees.

15. The inflatable cryo-ablation apparatus of claim 13, wherein the acute angle is sufficiently large such that no line extending radially from the central axis of the tubular member to an angled aperture extends completely through the angled aperture.

16. The inflatable cryo-ablation apparatus of claim 9, the tubular member defining about four to about ten angled apertures.

17. The inflatable cryo-ablation apparatus of claim 9, the plurality of angled apertures having a common inclination such that streams of coolant dispersed from the tubular member through the plurality of angled apertures swirl in the same direction around the outer surface of the tubular member and within the inner space defined by the first inflatable element.

18. The inflatable cryo-ablation apparatus of claim 9, further comprising a second inflatable element, the first inflatable element being positioned between the tubular member and the second inflatable element, wherein the tubular member, the first inflatable element and the second inflatable element are configured such that streams of coolant dispersed from the tubular element through the plurality of apertures swirl around the tubular member and within the inner space defined by the first inflatable element to inflate the first inflatable element and the second inflatable element.

19. The inflatable cryo-ablation apparatus of claim 9, the tubular member and the first inflatable member being configured such that a temperature along a circumferential section of the inner surface of the first inflatable element exposed to swirling coolant dispersed through the plurality of angled apertures is substantially constant.

20. The inflatable cryo-ablation apparatus of claim 9, the tubular member and the first inflatable member being configured such that a circumferential section of the inner surface of the first inflatable element is exposed to substantially the same amount of coolant.

* * * * *